(12) United States Patent
Hirose et al.

(10) Patent No.: US 8,487,298 B2
(45) Date of Patent: Jul. 16, 2013

(54) ORGANIC SEMICONDUCTOR TRANSISTOR

(75) Inventors: Hidekazu Hirose, Kanagawa (JP); Koji Horiba, Kanagawa (JP); Akira Imai, Kanagawa (JP); Takeshi Agata, Kanagawa (JP); Katsuhiro Sato, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 519 days.

(21) Appl. No.: 12/556,133

(22) Filed: Sep. 9, 2009

(65) Prior Publication Data

US 2010/0237332 A1    Sep. 23, 2010

(30) Foreign Application Priority Data

Mar. 23, 2009 (JP) ................................. 2009-070014

(51) Int. Cl.
*H01L 51/00* (2006.01)
(52) U.S. Cl.
USPC ...... 257/40; 257/642; 257/759; 257/E51.027; 257/E51.029
(58) Field of Classification Search
USPC ............ 257/40, 642, 759, E51.007, E51.027, 257/E51.028, E51.029; 438/99, 623, 725, 438/780
See application file for complete search history.

(56) References Cited

U.S. PATENT DOCUMENTS

| | | | |
|---|---|---|---|
| 5,574,291 A | 11/1996 | Dodabalapur et al. |
| 5,596,208 A | 1/1997 | Dodabalapur et al. |
| 5,659,181 A | 8/1997 | Bridenbaugh et al. |
| 5,946,551 A | 8/1999 | Dimitrakopoulos et al. |
| 5,981,970 A | 11/1999 | Dimitrakopoulos et al. |
| 6,107,117 A | 8/2000 | Bao et al. |
| 6,210,479 B1 | 4/2001 | Bojarczuk et al. |
| 6,278,127 B1 | 8/2001 | Dodabalapur et al. |
| 6,344,660 B1 | 2/2002 | Dimitrakopoulos et al. |
| 6,344,662 B1 | 2/2002 | Dimitrakopoulos et al. |
| 7,342,097 B2 | 3/2008 | Goddard et al. |

(Continued)

FOREIGN PATENT DOCUMENTS

| | | |
|---|---|---|
| JP | A-05-055568 | 3/1993 |
| JP | A-05-190877 | 7/1993 |

(Continued)

OTHER PUBLICATIONS

Gao et al, "Dibenzothiophene derivatives as new prototype semiconductors for organic field-effect transistors," J. Mater Chem., 2007, 17, pp. 1421-1426.*

(Continued)

*Primary Examiner* — Matthew Landau
*Assistant Examiner* — Colleen E Snow
(74) *Attorney, Agent, or Firm* — Oliff & Berridge, PLC

(57) ABSTRACT

An organic semiconductor transistor has plural electrodes and an organic semiconductor layer including at least one compound represented by the following Formula (I). In Formula (I), each R is independently a hydrogen atom or an alkyl group; and n and m are each independently an integer of from 1 to 3.

(I)

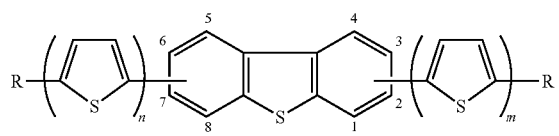

15 Claims, 2 Drawing Sheets

U.S. PATENT DOCUMENTS

| | | | |
|---|---|---|---|
| 7,863,600 B2* | 1/2011 | Nomoto | 257/40 |
| 2003/0077788 A1 | 4/2003 | Baker et al. | |
| 2007/0128764 A1 | 6/2007 | Tomino et al. | |
| 2008/0230776 A1 | 9/2008 | Li et al. | |

FOREIGN PATENT DOCUMENTS

| | | |
|---|---|---|
| JP | A-08-228034 | 9/1996 |
| JP | A-08-228035 | 9/1996 |
| JP | A-08-264805 | 10/1996 |
| JP | A-10-125924 | 5/1998 |
| JP | A-10-190001 | 7/1998 |
| JP | A-10-270712 | 10/1998 |
| JP | A-2000-174277 | 6/2000 |
| JP | A-2001-094107 | 4/2001 |
| JP | A 2006-339474 | 12/2006 |
| JP | A 2008-235517 | 10/2008 |

OTHER PUBLICATIONS

Voituriez et al, "Synthesis and electropolymerization of new sulfur-containing monomers," Synthetic Metals 146 (2004), pp. 139-143.*

Drury et al., "Low-cost all-polymer integrated circuits," *Applied Physics Letters*, 1998, vol. 73, No. 1, pp. 108-110.

Nov. 29, 2011 Decision of Refusal issued in Japanese patent application No. 2009-070014 (with translation).

* cited by examiner

ORGANIC SEMICONDUCTOR TRANSISTOR

CROSS REFERENCE TO RELATED APPLICATIONS

This application claims priority under 35 USC 119 from Japanese Patent Application No. 2009-070014, filed on Mar. 23, 2009.

BACKGROUND

1. Technical Field

The present invention relates to an organic semiconductor transistor.

2. Related Art

A thin film transistor is widely used as a switching element for display devices such as liquid crystal displays. Conventionally, the thin film transistor is made of amorphous or polycrystalline silicon.

In recent years, organic semiconductors represented by organic EL devices or the like have been studied extensively. At the same time, studies have been reported in which organic materials are incorporated in electronic circuits in place of silicon materials, owing to their advantages of light weight and flexibility.

SUMMARY

According to an aspect of the invention, there is provided an organic semiconductor transistor including plural electrodes and an organic semiconductor layer that includes at least one compound represented by the following Formula (I):

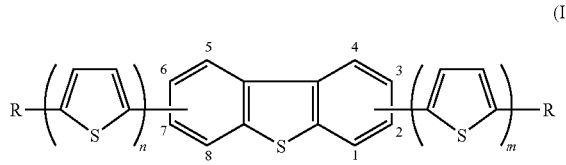

(I)

wherein, in Formula (I), each R is independently a hydrogen atom or an alkyl group; and n and m each is independently an integer of from 1 to 3.

BRIEF DESCRIPTION OF THE DRAWINGS

Exemplary embodiments of the present invention will be described in detail based on the following figures, wherein.

DETAILED DESCRIPTION

Figure 1:
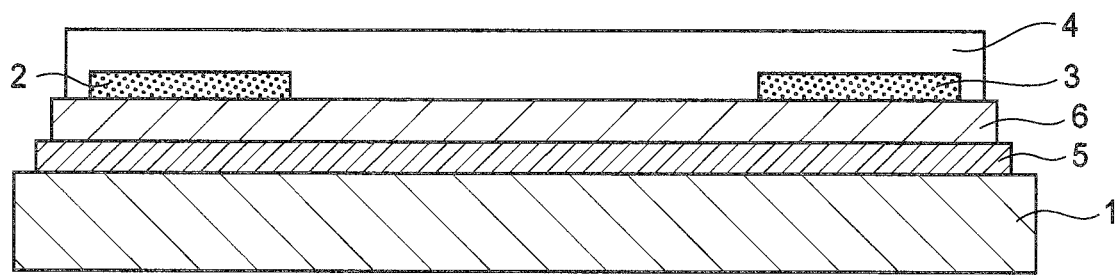
FIG. 1 is a schematic diagram showing an example of a layer configuration of an organic semiconductor transistor of an exemplary embodiment of the present invention.

Hereinafter, the exemplary embodiments of the present invention will be described in detail. Note that, the present invention is in no way limited by the action or function speculated in the present description.

The organic semiconductor transistor of the exemplary embodiments of the present invention at least has plural electrodes and an organic semiconductor layer that includes at least one compound represented by the following Formula (I). The compound represented by Formula (I) is described at first, and then the organic semiconductor transistor of the exemplary embodiments will be described.

Compound Represented by Formula (I)

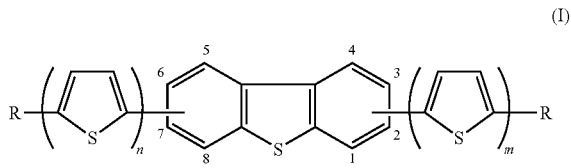

(I)

In Formula (I), each R is independently a hydrogen atom or an alkyl group; and n and m are each independently an integer of from 1 to 3.

The compound represented by Formula (I) has an excellent solubility in an organic solvent that is usually used in the preparation of electronic devices. Therefore, the organic semiconductor layer is formed in a so-called wet process by using a solution in which the compound represented by Formula (I) is dissolved in the organic solvent. In the thus-prepared organic semiconductor layer, owing to the excellent solubility of the compound represented by Formula (I) in the organic solvent, failures such as cracks, crazes, or chips in film formation may be suppressed. As a result, presumably defects in electrical properties are suppressed in the face of the film or unevenness in electrical properties is suppressed in the face. In addition, a device with a large area may be easily fabricated.

Furthermore, the compound that is represented by Formula (I) and has an excellent solubility is used stably over time. Therefore, the organic semiconductor transistor having an organic semiconductor layer containing the compound represented by Formula (I) provides stable electrical characteristics over time.

The compound represented by Formula (I) has a dibenzothiophene portion at the center thereof and thiophene rings on both ends of the dibenzothiophene portion. It is presumed that since the thiophene rings are incorporated into both ends, a n-electron conjugated system extends over a large area, thereby allowing charges to move easily and enhancing the charge mobility. Further, it is presumed that since a large number of sulfur atoms having a large ionic radius are incorporated, charge acceptance is increased and charge-injection property may be enhanced. As described above, the compound represented by Formula (I) is a material suitable for an organic semiconductor layer of a transistor.

Moreover, it is presumed that since the molecular weight of the compound represented by Formula (I) is increased by incorporating the thiophene rings, heat resistance is also increased.

Note that, in the present description, "thiophene ring(s)" means a thiophene ring group or plural thiophene rings that are linked to each other.

Hereinafter, the compound represented by Formula (I) will be described in detail.

In Formula (I), each R is independently a hydrogen atom or an alkyl group.

The alkyl group represented by R is an alkyl group having preferably from 1 to 20 carbon atoms, more preferably from 1 to 12 carbon atoms, and still more preferably from 3 to 8 carbon atoms.

The alkyl group represented by R may be any alkyl group of straight-chain, branched, or cyclic, and from the viewpoint of synthesis, solubility and film forming property, the alkyl group is preferably a straight-chain or branched alkyl group.

Specific examples of the alkyl group represented by R may include a methyl group, an ethyl group, a n-propyl group, an i-propyl group, a n-butyl group, a t-butyl group, a n-hexyl group, a n-octyl group, a n-dodecyl group, and a n-octadecyl group, preferably a methyl group, an ethyl group, a n-propyl group, an i-propyl group, a n-butyl group, a n-hexyl group, a n-octyl group, and a n-dodecyl group, and more preferably a n-propyl group, an i-propyl group, a n-butyl group, a n-hexyl group, and a n-octyl group.

R in Formula (I) is preferably a hydrogen atom or an unsubstituted alkyl group, more preferably a hydrogen atom or an unsubstituted straight-chain alkyl group, still more preferably a hydrogen atom or an unsubstituted straight-chain alkyl group having from 1 to 20 carbon atoms, still more preferably a hydrogen atom or an unsubstituted straight-chain alkyl group having from 1 to 12 carbon atoms, and still more preferably a hydrogen atom or an unsubstituted straight-chain alkyl group having from 3 to 8 carbon atoms.

The two Rs in Formula (I) may be the same as or different from each other, but from the viewpoint of production, preferably the same.

In Formula (I), n and m each independently represents an integer of from 1 to 3, preferably from 2 to 3, and from the viewpoint of appropriateness in ionization potential or solubility in solvent, more preferably 2.

In Formula (I), n and m may be the same as or different from each other, but from the viewpoint of production, preferably the same.

In Formula (I), the linking positions of the two thiophene rings are not particularly limited, but from the viewpoint of synthesis, they may be linked preferably at 1 and 8, 2 and 7, 3 and 6, or 4 and 5.

In particular, considering the solubility in an organic solvent, a dibenzothiophene compound that has thiophene rings at the positions of 2 and 7 and is represented by the following Formula (II) and a dibenzothiophene compound that has thiophene rings at the positions of 3 and 6 and is represented by the following Formula (III) are preferable.

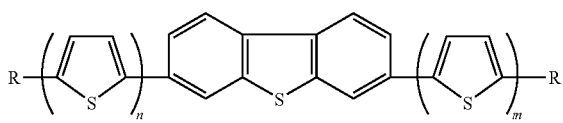

(II)

In Formula (II), each R is independently a hydrogen atom or an alkyl group and has the same meaning as the R in Formula (I), and the preferable range thereof is also the same.

In Formula (II), n and m each is independently an integer of from 1 to 3 and has the same meaning as the n and m in Formula (I), and the preferable range thereof is also the same.

The compound represented by Formula (II) has a high crystallinity, so that it is preferable from the viewpoint of preparing an organic semiconductor layer having uniform electrical characteristics. In addition, atmospheric stability such as stability against oxygen may be enhanced.

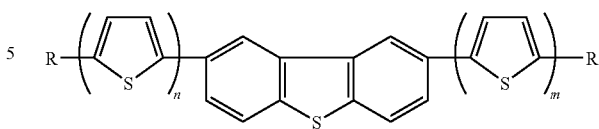

(III)

In Formula (III), each R is independently a hydrogen atom or an alkyl group and has the same meaning as the R in Formula (I), and the preferable range thereof is also the same.

In Formula (III), n and m each is independently an integer of from 1 to 3 and has the same meaning as the n and m in Formula (I), and the preferable range thereof is also the same.

The molecular structure of the compound represented by Formula (II) has a large steric hindrance, providing a still more excellent solubility.

Specific examples of the compound represented by Formula (I) are described below, but they are not limitative.

| Structure | R | n | m | Linking positions |
|---|---|---|---|---|
| 1 | H | 1 | 1 | 2, 7 |
| 2 | H | 1 | 1 | 3, 6 |
| 3 | H | 2 | 1 | 2, 7 |
| 4 | H | 2 | 2 | 3, 6 |
| 5 | H | 3 | 1 | 2, 7 |
| 6 | H | 3 | 2 | 3, 6 |
| 7 | n-$C_3H_7$ | 1 | 1 | 2, 7 |
| 8 | n-$C_3H_7$ | 2 | 2 | 3, 6 |
| 9 | n-$C_3H_7$ | 2 | 2 | 2, 7 |
| 10 | n-$C_3H_7$ | 2 | 1 | 2, 7 |
| 11 | t-Bu | 1 | 1 | 2, 7 |
| 12 | t-Bu | 1 | 1 | 3, 6 |
| 13 | t-Bu | 2 | 2 | 3, 6 |
| 14 | n-$C_6H_{13}$ | 1 | 1 | 2, 7 |
| 15 | n-$C_6H_{13}$ | 1 | 1 | 3, 6 |
| 16 | n-$C_6H_{13}$ | 2 | 2 | 2, 7 |
| 17 | n-$C_6H_{13}$ | 2 | 1 | 2, 7 |
| 18 | n-$C_6H_{13}$ | 2 | 2 | 3, 6 |
| 19 | n-$C_6H_{13}$ | 2 | 1 | 3, 6 |
| 20 | n-$C_6H_{13}$ | 2 | 2 | 2, 7 |
| 21 | n-$C_6H_{13}$ | 1 | 3 | 2, 7 |
| 22 | n-$C_8H_{17}$ | 1 | 1 | 2, 7 |
| 23 | n-$C_8H_{17}$ | 1 | 2 | 3, 6 |
| 24 | n-$C_8H_{17}$ | 2 | 2 | 2, 7 |
| 25 | n-$C_8H_{17}$ | 2 | 2 | 3, 6 |
| 26 | n-$C_{12}H_{25}$ | 1 | 1 | 2, 7 |
| 27 | n-$C_{12}H_{25}$ | 1 | 1 | 3, 6 |
| 28 | n-$C_{12}H_{25}$ | 2 | 1 | 2, 7 |
| 29 | n-$C_{12}H_{25}$ | 2 | 2 | 3, 6 |
| 30 | n-$C_{12}H_{25}$ | 3 | 3 | 2, 7 |

For the synthesis of the compound represented by Formula (I), biaryl cross-coupling reactions may be used. The biaryl cross-coupling reactions may include Suzuki reaction, Kharasch reaction, Negishi reaction, Stille reaction, Grignard reaction, and Ullmann reaction.

For instance, the following synthesis method is quoted, but it is not limitative.

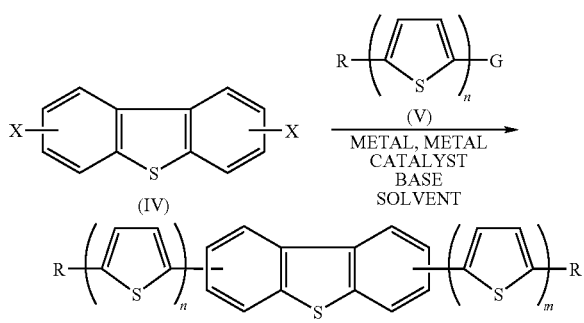

In Formulae (IV) and (V), Xs and G each are independently a halogen atom, B(OH)$_2$, or any one of the following.

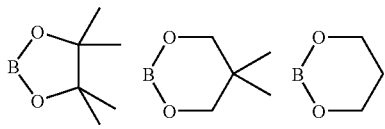

For the synthesis, a metal or metal complex catalyst a base, a solvent, or an auxiliary catalyst such as an organic phosphine ligand may be used.

Examples of the metal catalyst include Pd, Cu, Ti, Sn, Ni, and Pt.

Examples of the metal complex catalyst include tetra(t-riphenyl phosphine) palladium (Pd(P(C$_6$H$_5$)$_3$)$_4$), diacetoxy palladium (Pd(OCOCH$_3$)$_2$), tris(dibenzylidene acetone) dipalladium (Pd$_2$(dba)$_3$), di(triphenyl phosphine)dichloro palladium (Pd(P(C$_6$H$_5$)$_3$)$_2$Cl$_2$), dichloro(1,2-bis(diphenylphosphino)ferrocenyl palladium (Pd(dppf)$_2$Cl$_2$), Pd/C, and nickel acetylacetonate (Ni(acac)$_2$).

Examples of the base include: an inorganic base such as sodium carbonate (Na$_2$CO$_3$), potassium carbonate (K$_2$CO$_3$), cesium carbonate (Cs$_2$CO$_3$), or barium hydroxide (Ba (OH)$_2$); and an organic base such as triethylamine (N (C$_2$H$_5$)$_3$), diisopropylamine (NH(CH$_3$)$_2$CH)$_2$), diethylamine (NH(C$_2$H$_5$)$_2$), dimethylamine (NH(CH$_3$)$_2$), trimethylamine (N(CH$_3$)$_3$), 1,8-diazabicyclo[5.4.0]-7-undecene (DBU), N,N-dimethyl-4-aminopyridine (DMAP), or pyridine.

Regarding the solvent, any solvent may be used as long as it does not significantly inhibit the reaction. Examples of the solvent include: an aromatic hydrocarbon solvent such as benzene, toluene, xylene, or mesitylene; an ether solvent such as diethyl ether, tetrahydrofuran, or dioxane; acetonitrile; dimethylformamide; dimethylsulfoxide; methanol; ethanol; isopropyl alcohol; and water.

Examples of the auxiliary catalyst such as an organic phosphine ligand include triphenyl phosphine (PPh$_3$), tri-o-tolyl phosphine (P-(o-CH$_3$C$_6$H$_4$)$_3$), tributyl phosphine (P(C (CH$_3$)$_3$)$_3$), and triethyl phosphine (P(C$_2$H$_5$)$_3$).

The above synthesis reaction is carried out in an inert gas atmosphere such as nitrogen or argon. The reaction may be carried out either at a normal pressure or under a pressurized condition.

The reaction temperature ranges from 20° C. to 300° C. and preferably from 50° C. to 180° C. The reaction time may depend on the reaction conditions, but may be selected in the range of from several minutes to 20 hours.

The amount of the metal or metal complex catalyst to be used is not particularly limited, but may range from 0.001 mol % to 10 mol %, and more preferably from 0.01 mol % to 5.0 mol %, with respect to the compound represented by Formula (IV).

The amount of the base to be used ranges from 0.5 mol % to 4.0 mol %, and more preferably from 1.0 mol % to 2.5 mol %, with respect to the compound represented by Formula (IV).

After the reaction, the reaction solution is put into water, stirred, and, when the reaction product is crystals, filtered off, thereby obtaining a crude product. When the reaction product is oily, the crude product is obtained by subjecting the reaction product to extraction with a solvent such as ethyl acetate or toluene. The thus-obtained crude product is subjected to column purification with silica gel, alumina, activated earth, or active carbon, or these adsorbents are added to a solution of the crude product so as to adsorb insoluble substances. Further, when the reaction product is crystals, these crystals are purified by recrystallization in a solvent such as hexane, methanol, acetone, ethanol, ethyl acetate, or toluene. Furthermore, the purity may be increased by column chromatography, purification by sublimation, or the combination thereof.

Organic Semiconductor Transistor

The organic semiconductor transistor of the exemplary embodiments of the present invention at least has plural electrodes and an organic semiconductor layer that includes at least one compound represented by Formula (I). As long as this configuration is satisfied, the other configuration is not particularly limited.

Hereinafter, with reference to the accompanied figures, more detailed description will be made, but the description is not limitative.

Figure 2:
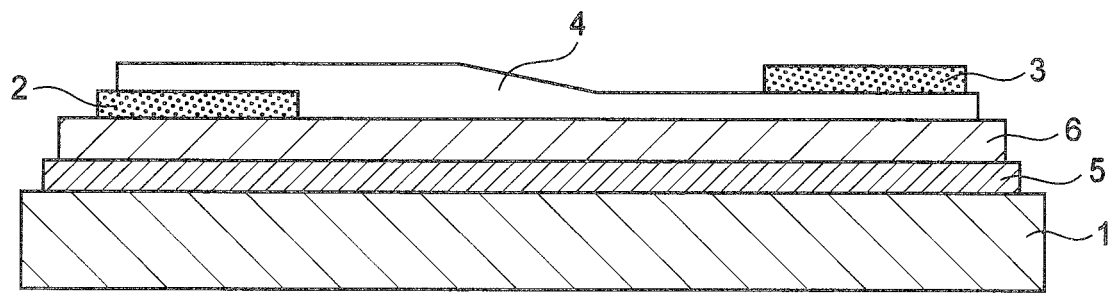
FIG. 2 is a schematic diagram showing an example of a layer configuration of an organic semiconductor transistor of another exemplary embodiment of the present invention.
Figure 3:
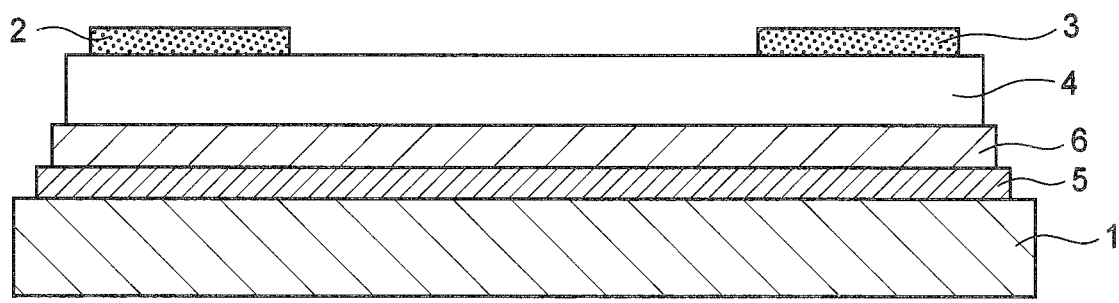
FIG. 3 is a schematic diagram showing an example of a layer configuration of an organic semiconductor transistor of still another exemplary embodiment of the present invention.
Figure 4:
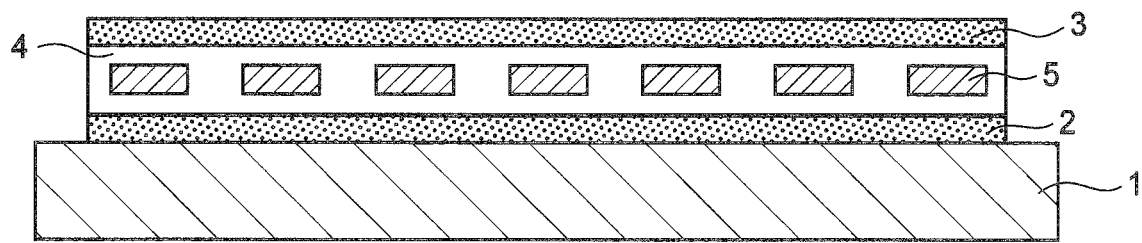
FIG. 4 is a schematic diagram showing an example of a layer configuration of an organic semiconductor transistor of still another exemplary embodiment of the present invention.

FIGS. 1, 2, 3, and 4 show cross-sectional views illustrating the configuration of examples of the organic semiconductor transistors of the exemplary embodiments of the present invention. FIGS. 1, 2, and 3 show field effect transistors. FIG. 4 shows a static induction transistor.

The field effect transistors shown in FIGS. 1, 2, and 3, each has a source electrode 2 and a drain electrode 3 that are disposed in a manner that they are separated from each other with a distance therebetween, an organic semiconductor layer 4 that is in contact with both of the source electrode 2 and the drain electrode 3, a gate electrode 5 that is separated from both of the source electrode 2 and the drain electrode 3, and an insulation layer 6 that is sandwiched between the organic semiconductor layer 4 and the gate electrode 5.

The field effect transistors are one mode of transistors that are widely used presently, having advantages of high speed switching performance, simplicity in production processes, and suitability for integration.

In the field effect transistors shown in FIGS. 1, 2, and 3, the current that passes from the source electrode 2 to the drain electrode 3 is regulated by the voltage applied to the gate electrode 5.

The organic semiconductor transistor shown in FIG. 1 has the gate electrode 5 on a substrate 1 and further has the insulation layer 6 on the gate electrode 5. On the insulation layer 6, the source electrode 2 and the drain electrode 3 are formed in a manner that they are separated from each other with a distance therebetween. The portions of insulation layer 6 that are exposed out of the source electrode 2 and the drain electrode 3 are covered with the organic semiconductor layer 4.

In the organic semiconductor transistor shown in FIG. 2, either one of the source electrode 2 and the drain electrode 3 is formed on the insulation layer 6; the organic semiconductor layer 4 is formed in a manner that the organic semiconductor layer 4 covers the source electrode 2 or the drain electrode 3 that is formed on the insulation layer 6 and the insulation layer 6; and the rest of the source electrode 2 and drain electrode 3 that is not formed on the insulation layer 6 is formed on the organic semiconductor layer 4 so as to sandwich the organic semiconductor layer 4 between the source electrode 2 or drain electrode 3 and the insulation layer 6. FIG. 2 specifically shows, as an example, a case in which the source electrode 2 is formed on the insulation layer 6, on which the organic semiconductor layer 4 is provided, and the drain electrode 3 is formed on the organic semiconductor layer 4, so that part of the organic semiconductor layer 4 is sandwiched between the insulation layer 6 and the drain electrode 3.

In the organic semiconductor transistor shown in FIG. 3, the organic semiconductor layer 4 is formed on the insulation layer 6, and the source electrode 2 and the drain electrode 3 are formed on the organic semiconductor layer 4 in a manner that they are separated from each other with a distance therebetween.

The static induction transistor shown in FIG. 4 has the source electrode 2 and the drain electrode 3 provided facing each other, the organic semiconductor layer 4 that is in contact with both of the source electrode 2 and the drain electrode 3 and sandwiched between the source electrode 2 and the drain electrode 3, and the gate electrodes 5 that are separated from both of the source electrode 2 and the drain electrode 3. Namely, the static induction transistor has, on the substrate 1, the source electrode 2, the organic semiconductor layer 4, and the drain electrode 3 in this order, and has plural gate electrodes 5 in the organic semiconductor layer 4. The gate electrodes 5 are disposed parallel to both of the source electrode 2 and the drain electrode 3 in a direction perpendicular to the paper surface, and each of the gate electrodes 5 are also disposed parallel to each other.

In the organic semiconductor transistors shown in FIGS. 1, 2, 3, and 4, the current that passes from the source electrode 2 to the drain electrode 3 is regulated by the voltage applied to the gate electrode 5.

As the material used for each electrode, materials which allow charges to be injected efficiently are used, and examples thereof include metals, metal oxides, electroconductive polymers, carbon, and graphite.

Examples of the metal used for the electrodes include magnesium, aluminum, gold, silver, copper, platinum, chromium, tantalum, indium, palladium, lithium, calcium, and the alloys thereof. Examples of the metal oxide include lithium oxide, magnesium oxide, aluminum oxide, indium tin oxide (ITO), tin oxide (NESA), indium oxide, zinc oxide, and indium zinc oxide, and a metal oxide film formed from any of these metal oxide may be used.

Examples of the electroconductive polymer used for the electrodes include polyaniline, polythiophene, polythiophene derivatives, polypyrrole, polypyridine, and a complex of polyethylene dioxythiophene and polystyrene sulfonic acid.

Note that, in the exemplary embodiments of the present invention, "electroconductive" means that the volume resistivity is in the range of $10^7$ Ωcm or lower. On the other hand, "insulating" means that the volume resistivity is in the range of $10^{14}$ Ωcm or higher.

The volume resistivity is measured in accordance with a known test method of thermosetting plastic (JIS-K6911 (1995)) as follows. Specifically, a voltage of 100 volt is applied by using a circular electrode (a UR probe of HIRESTOR IP (trade name, manufactured by Mitsubishi Chemical Corporation): the cylindrical electrode has an outside diameter of 16 mm, the inside diameter of a ring electrode is 30 mm, and the outside diameter of the ring electrode is 40 mm) in an environment of 22° C. and 55% RH; 5 seconds later, the current is measured using R8340A ULTRA HIGH RESISTANCE METER (trade name, manufactured by ADVANTEST CORP.); volume resistance is obtained from the measured current value; and the volume resistivity is calculated from the volume resistance.

The difference between the ionization potential of the material used for the drain electrode 3 and the source electrode 2 and the ionization potential of the compound that is represented by Formula (I) and is used for the organic semiconductor layer 4 is preferably 1.0 eV or less, and particularly preferably 0.5 eV or less, from the viewpoint of charge injection characteristics.

Considering the difference between the ionization potentials of these electrodes and the compound represented by Formula (I), Au is preferably used as the electrode material.

Note that, when an electroconductive substrate is used, for instance, in the case of a highly doped silicon substrate, the substrate may also serve as the gate electrode.

Examples of the method of forming the electrodes include: a process in which a film of the above material is formed by vacuum evaporation or sputtering, and then the resulting thin film is formed into electrodes by a conventional photolithographic or lift-off technique; a process in which aluminum or the like is heat transferred; and a process in which a resist layer is formed by an ink-jet technique or the like, and then the resulting resist layer is etched. In still another process, an electroconductive polymer may be dissolved in a solvent, and the resulting solution may be subjected to patterning using the ink-jet technique or the like.

The thickness of the source electrode 2 or the drain electrode 3 is not particularly limited, but usually preferably ranges from several nm to several hundred μm, more preferably from 1 nm to 100 μm, still more preferably from 10 nm to 10 μm.

The distance (channel length) between the source electrode 2 and the drain electrode 3 usually ranges preferably from several hundred nm to several mm, and more preferably from 1 μm to 1 mm.

The insulation layer 6 may be formed from an inorganic material such as silicon dioxide, silicon nitride, tantalum oxide, aluminum oxide, titanium oxide, tin oxide, vanadium oxide, or strontium barium titanate; an organic insulating polymer such as polycarbonate resin, polyester resin, methacrylic resin, acrylic resin, polyvinylchloride resin, cellulose resin, urethane resin, epoxy resin, polystyrene resin, polyvinylacetate resin, a styrene-butadiene copolymer, a vinylidene chloride-acrylonitrile copolymer, a vinylchloride-vinylacetate-maleic anhydride copolymer, or silicone resin; and the like, but they are not limited.

Examples of the method of forming the insulation layer of the inorganic material include a dry process such as vacuum evaporation, molecular beam epitaxial growth, ion-clusterbeam method, low energy beam method, ion plating method, CVD, sputtering, and atmospheric pressure plasma method; and a wet process such as spray coating, spin coating, blade coating, dip coating, casting, roll coating, bar coating, die coating, the air-knife method, or the ink-jet method. Any of these methods may be selected in accordance with the material used and the characteristics of the objective devices.

As the method of forming the insulation layer in which the organic insulating polymer is used, the above wet process may be preferably used.

The thickness of the insulation layer 6 is not particularly limited, but usually ranges preferably from several nm to several hundred μm, more preferably from 1 nm to 100 μm, and still more preferably from 10 nm to 10 μm.

Additionally, the interface of the insulation layer 6 that is in contact with the organic semiconductor layer 4 may be treated with, for example, a silane compound such as hexamethyl disilazane, octadecyl trimethoxysilane, octadecyl trichlorosilane, or octyl trichlorosilane. In the case of an organic insulation layer, the layer may be subjected to a rubbing treatment.

Examples of the substrate 1 include a substrate of silicon single crystal highly doped with phosphorus or the like, a glass substrate, and a substrate of plastics such as polycarbonate resin, polyester resin, methacrylic resin, acrylic resin, polyvinylchloride resin, cellulose resin, urethane resin, epoxy resin, polystyrene resin, polyvinylacetate resin, a styrene-butadiene copolymer, a vinylidene chloride-acrylonitrile copolymer, a vinylchloride-vinylacetate-maleic anhydride copolymer, or silicone resin, but these are not limitative.

Particularly, when the organic semiconductor transistor of the exemplary embodiments of the present invention is used in an electronic circuit that is used for electronic or digital paper or portable electronic devices, a flexible substrate is preferably used as the substrate 1. In particular, a flexible substrate having a bending elastic modulus of at least 1,000 MPa may provide a still more flexible driving circuit or electronic circuit for display devices.

Examples of the method of forming the organic semiconductor layer 4 include a wet printing process including spin coating, casting, dip coating, die coating, roll coating, bar coating, and the ink-jet method.

As described above, the compounds represented by Formulae (I), (II), and (III) exhibit an excellent solubility in an organic solvent. Therefore, the wet process of forming an organic semiconductor layer using a solution in which any of these compounds is dissolved is a preferable process of forming an organic semiconductor that includes any of the compounds represented by Formulae (I), (II), and (III).

Examples of the solvent used for the coating liquid include: water; alcohols such as methanol, ethanol, isopropyl alcohol, or butanol; ketone solvents such as acetone, methyl ethyl ketone, methyl isobutyl ketone, or cyclohexanone; ester solvents such as ethyl acetate or butyl acetate; hydrocarbon solvents such as hexane, octane, toluene, xylene, ethylbenzene, or cumene; halogenated hydrocarbon solvents such as dichloromethane, chloroform, dichloroethane, tetrachloroethylene, chlorobenzene, o-dichlorobenzene, or trichlorobenzene; nitrile solvents such as acetonitrile, propionitrile, methoxyacetonitrile, glutarodinitrile, or benzonitrile; and aprotic polar solvents such as dimethylsulfoxide, sulfolane, N,N-dimethylformamide, N,N-dimethylacetamide, or N-methyl-2-pyrrolidone, but these are not limitative. These solvents may be used singly, or in combination of two or more thereof.

The thickness of the organic semiconductor layer 4 is not particularly limited, but may range preferably from several nm to several hundred μm, more preferably from 1 nm to 100 μm, and still more preferably from 5 nm to 10 μm.

The organic semiconductor layer 4 may be doped. Either of a donor dopant or an acceptor dopant may be used.

As the donor dopant, a compound that is capable of donating electrons to the organic compound of the organic semiconductor layer 4 may be preferably used. Examples of the donor dopant include: an alkali metal such as Li, Na, K, Rb, or Cs; an alkaline earth metal such as Ca, Sr, or Ba; a rare earth metal such as Y, La, Ce, Pr, Nd, Sm, Eu, Gd, Tb, Dy, Ho, Er, or Yb; and ammonium ion.

As the acceptor dopant, a compound that is capable of eliminating electrons from the organic compound of the organic semiconductor layer 4 may be preferably used. Examples of the acceptor dopant include: a halogen compound such as $Cl_2$, $Br_2$, $I_2$, ICl, $ICl_3$ or IBr; a Lewis acid such as $PF_5$, $AsF_6$, $SbF_5$, $BF_3$, or $SO_3$; a protonic acid such as HF, HCl, $HNO_3$, or $H_2SO_4$; an organic acid such as acetic acid, formic acid, or amino acid; a transition metal compound such as $FeCl_3$, $TiCl_4$, or $HfCl_4$; an electrolyte anion such as $Cl^-$, $Br^-$, $I^-$, $ClO_4^-$, or sulfonic acid anion; and an organic compound such as tetracyanoethylene, 7,7,8,8-tetracyanoquinodimethane, 11,11,12,12-tetracyanonaphto-2,6-quinodimethane, 2,5-difluoro-7,7,8,8-tetracyanoquinodimethane, or tetrafluorotetracyanoquinodimethane.

Furthermore, in order to prevent degradation of the organic semiconductor transistor caused by water or oxygen, a protective layer may be provided. Specific examples of the material for the protective layer include: metals such as In, Sn, Pb, Au, Cu, Ag, or Al; metal oxides such as MgO, $SiO_2$, or $TiO_2$; and resins such as polyethylene resin, polyurea resin, or polyimide resin. The protective layer may be formed by vacuum evaporation, sputtering, plasma polymerization, CVD, or coating method.

In the organic semiconductor transistor of the exemplary embodiments of the present invention, the compound represented by Formula (I) is used for the organic semiconductor layer. The compound represented by Formula (I) exhibits an excellent solubility in an organic solvent that is generally used in the fabrication of electronic devices. Therefore, when the compound represented by Formula (I) is used for the organic semiconductor layer, the organic semiconductor layer can be produced in a wet process, which enables formation of an organic semiconductor layer using inexpensive apparatus or the like as compared with the case in which a layer is formed by sputtering or the like, and which enables easy production of a device having a large area. In addition to that, in the organic semiconductor layer that includes the compound represented by Formula (I) and is formed in a wet process, failures such as cracks, crazes, or chips are suppressed in the process of forming the layer, thereby suppressing defects or unevenness in electrical properties in the face of the layer. Furthermore, an organic semiconductor transistor having stable electrical characteristics over time is provided.

When an electronic device using the organic semiconductor transistor of the exemplary embodiments of the present invention is fabricated, a configuration (semiconductor unit) having, on a support, at least one organic semiconductor transistor of the exemplary embodiments of the present invention incorporated therein may be used, and the semiconductor unit may be combined with the other elements, circuits, and the like so as to fabricate a desired electronic device.

EXAMPLES

Hereinafter, the present invention will be further described with reference to the following examples, but it should be construed that the invention is in no way limited to those examples.

For the identification of objective products, $^1$H-NMR spectra ($^1$H-NMR, solvent: $CDCl_3$, UNITY-300 manufactured by VARIAN Corp., 300 MHz) and IR spectra (KBr tablet method, a fourier transform infrared (FT-IR) spectrometer (FT-730, manufactured by HORIBA Ltd., resolution: 4 cm-1) are used.

Synthesis Example 1

Exemplary Compound 16

In a nitrogen gas atmosphere, a mixed solution containing tetra(triphenylphosphine) palladium (0.069 g), 2,7-dibromodibenzothiophene (0.325 g), 2-hexylbithiophene boronic acid ester (0.725 g), toluene (6 mL), a 1M sodium hydrogen carbonate aqueous solution (4 mL), and ethanol (2 mL) is refluxed and agitated for 3 hours; and after toluene (20 mL) is added, the mixed solution is further refluxed for 2 hours. The resulting precipitates are separated by suction filtration and are subjected to Soxhlet extraction with toluene, thereby obtaining 0.346 g of Exemplary Compound 16, which is identified by the $^1$H-NMR and FT-IR measurement.

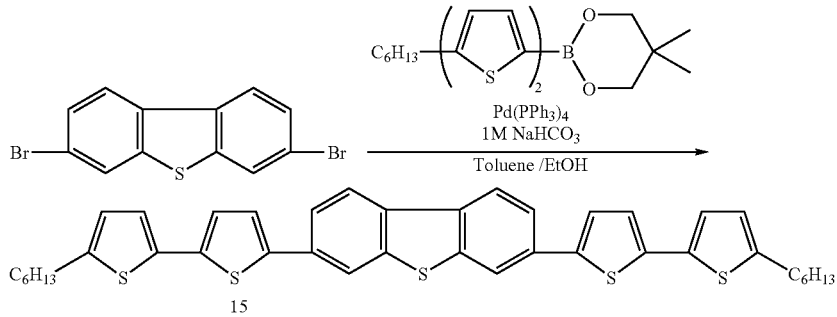

Synthesis Example 2

Exemplary Compound 18

In a nitrogen gas atmosphere, a mixed solution containing tetra(triphenylphosphine) palladium (0.104 g), 3,6-dibromodibenzothiophene (0.502 g), 2-hexylbithiophene boronic acid ester (1.20 g), toluene (6 mL), a 1M sodium hydrogen carbonate aqueous solution (6 mL), and ethanol (4 mL) is refluxed and agitated for 7 hours. The resulting precipitates are separated by suction filtration and are recrystallized in a mixed solvent of toluene and ethanol (toluene:ethanol=2:1 (volume ratio)), thereby obtaining 0.787 g of Exemplary Compound 18, which is identified by the $^1$H-NMR and FT-IR measurement.

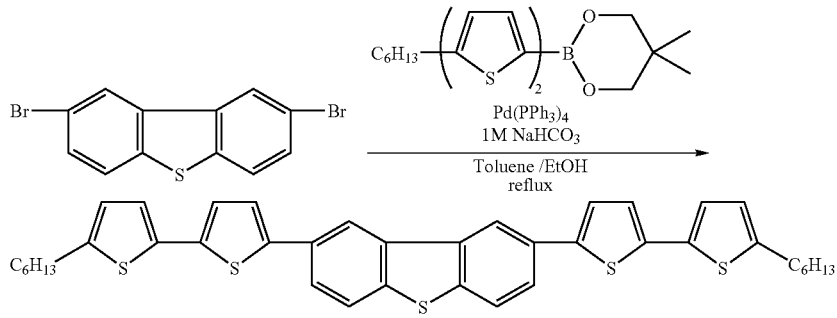

Synthesis Example 3

Exemplary Compound 14

In a nitrogen gas atmosphere, a mixed solution containing tetra(triphenylphosphine) palladium (0.069 g), 2,7-dibromodibenzothiophene (0.342 g), 2-hexylthiophene boronic acid ester (0.725 g), toluene (4 mL), a 1M sodium hydrogen carbonate aqueous solution (4 mL), and ethanol (2 mL) is refluxed and agitated for 5 hours. The resulting precipitates are separated by suction filtration and are recrystallized in a mixed solvent of hexane and tetrahydrofuran (THF) (hexane:THF=1:1 (volume ratio)), thereby obtaining 0.387 g of Exemplary Compound 14, which is identified by the $^1$H-NMR and FT-IR measurement.

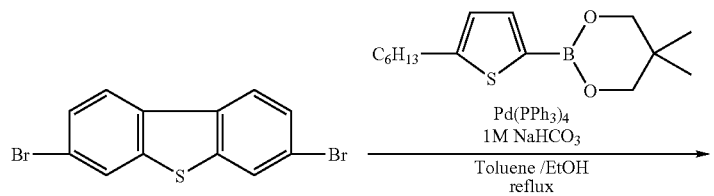

-continued

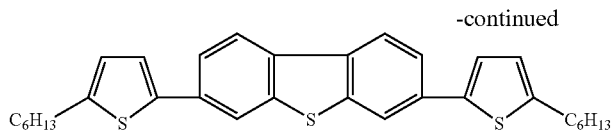

Example 1

On a silicon substrate having an electrical resistivity of 0.007 Ω·cm, which also serves as a gate electrode, a 200 nm-thick SiO$_2$ film is formed by thermal oxidation, which serves as an insulation film.

On the insulation film, a 10 nm-thick titanium film and a 100 nm-thick gold film are formed by vacuum evaporation, and they are subjected to patterning by photolithography, to form a source electrode and a drain electrode. The channel length from the source electrode to the drain electrode is 25 μm, and the channel width is 1 mm.

After that, the silicon substrate is subjected to 2 minute ultrasonic cleaning in an electronic grade acetone, 2 minute ultrasonic cleaning in an electronic grade 2-propanol, drying with a dry nitrogen gas, and 15 minute UV-ozone irradiation so as to clean the surface of the silicon substrate.

Exemplary Compound 16 in an amount of 0.4% by mass is dissolved in an electronic grad toluene. The resulting solution is applied on the cleaned silicon substrate by drop coating. After the coating is left for drying, it is heated in a nitrogen gas atmosphere at 100° C. for 1 minute to obtain an organic semiconductor layer. In this way, an organic semiconductor transistor is fabricated. The resulting organic semiconductor layer has a thickness of 85 nm.

The organic semiconductor transistor fabricated as described above exhibits p-type transistor characteristics.

Measurement of Charge Mobility

Charge mobility is obtained from the saturation region of the current to voltage characteristics of the resulting transistor. In addition, the transistor is stored at 25° C. for one month, and after that, the characteristics of the transistor are evaluated so as to measure the charge mobility again. The results are shown in Table 1.

Film Formability

An area of 1 mm×1 mm of the surface of the above prepared organic semiconductor layer is observed with an optical microscope so as to find failures such as cracks, crazes, or chips. The results are shown in Table 1. The evaluation criteria are shown below. Further, the film formability is also evaluated for the case where the solvent is replaced from toluene to tetrahydrofuran.

Evaluation Criteria for Film Formability

The following criteria are used for the evaluation of the results observed with the microscope.

A: The surface is entirely covered with the film, which means excellent film formability.

B: Portions that are not partially covered with the film are observed.

C: A number of portions that are not covered with the film are observed.

Examples 2 and 3

Organic semiconductor transistors are fabricated in substantially similar manner to that in Example 1, except that Exemplary Compound 16 that is used to form the organic semiconductor layer in Example 1 is replaced with Exemplary Compound 18 and Exemplary Compound 14, respectively. The resulting organic semiconductor transistors are evaluated in substantially similar manner to that in Example 1.

Comparative Examples 1 and 2

In Comparative Example 1, an organic semiconductor transistor is fabricated in substantially similar manner to that in Example 1, except that 13,6-N-sulfinylacetamide pentacene (manufactured by Aldrich Corp.) is used in place of Exemplary Compound 16 and that the heating temperature is changed to 160° C.

In Comparative Example 2, an organic semiconductor transistor is fabricated in substantially similar manner to that in Comparative Example 1, except that poly(3-hexylthiophene) (manufactured by Aldrich Corp.) is used in place of 13,6-sulfinylacetoamide pentacene used in Comparative Example 1 and that the solvent is changed to chloroform.

The organic semiconductor transistors of Comparative Examples 1 and 2 are evaluated in substantially similar manner to that in Example 1. The results are shown in Table 1.

TABLE 1

| | Charge mobility (cm$^2$/Vs) | | Film formability | |
|---|---|---|---|---|
| | Immediately after fabrication | 1 month later after fabrication | Toluene | Tetrahydrofuran |
| Example 1 | 6.28 × 10$^{-4}$ | 9.48 × 10$^{-5}$ | A | A |
| Example 2 | 4.58 × 10$^{-4}$ | 5.37 × 10$^{-5}$ | A | A |
| Example 3 | 7.86 × 10$^{-4}$ | 1.25 × 10$^{-4}$ | A | A |
| Comparative Example 1 | 7.5 × 10$^{-5}$ | Unmeasurable | B | A |
| Comparative Example 2 | 3.5 × 10$^{-5}$ | 9.3 × 10$^{-7}$ | B (chloroform) | A |

Table 1 shows that the organic semiconductor transistors of Examples 1, 2, and 3, as compared with the organic semiconductor transistors of Comparative Examples 1 and 2, have high charge mobilities immediately after the fabrication and also exert stable charge mobilities even one month after the fabrication.

The organic semiconductor layers of Examples 1, 2, and 3, as compared with the organic semiconductor layers of Comparative Examples 1 and 2, have excellent film formabilities, and failures such as cracks therein are suppressed.

The foregoing description of the embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An organic semiconductor transistor comprising:
a plurality of electrodes; and
an organic semiconductor layer including at least one compound represented by the following Formula (I),

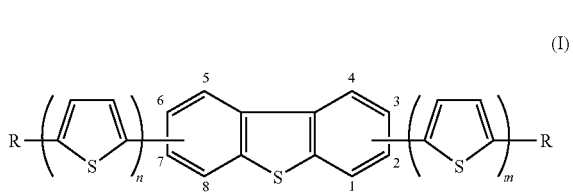

wherein, in Formula (I),
each R is independently a hydrogen atom or an alkyl group; and
n and m are each an integer of 2.

2. The organic semiconductor transistor according to claim 1, wherein the alkyl group is an alkyl group having 1 to 20 carbon atoms.

3. The organic semiconductor transistor according to claim 1, wherein the alkyl group is a straight-chain or branched alkyl group.

4. The organic semiconductor transistor according to claim 1, wherein the two Rs in Formula (I) are the same.

5. The organic semiconductor transistor according to claim 1, wherein, in Formula (I), the two thiophene rings are linked at 1 and 8, 2 and 7, 3 and 6, or 4 and 5.

6. The organic semiconductor transistor according to claim 1, wherein the compound represented by Formula (I) is a compound represented by the following Formula (II):

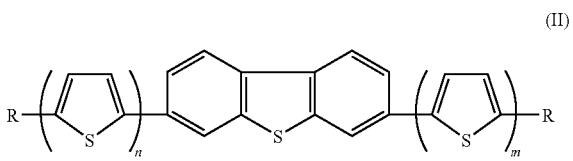

wherein, in Formula (II),
each R is independently a hydrogen atom or an alkyl group; and
n and m are each an integer of 2.

7. The organic semiconductor transistor according to claim 6, wherein the alkyl group is an alkyl group having 1 to 20 carbon atoms.

8. The organic semiconductor transistor according to claim 6, wherein the alkyl group is a straight-chain or branched alkyl group.

9. The organic semiconductor transistor according to claim 6, wherein the two Rs in Formula (II) are the same.

10. The organic semiconductor transistor according to claim 1, wherein the compound represented by Formula (I) is a compound represented by the following Formula (III):

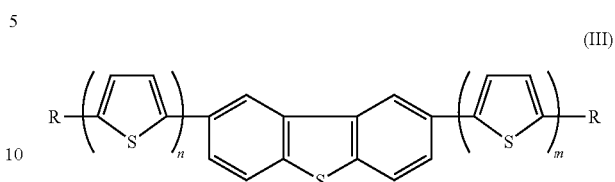

wherein, in Formula (III),
each R is independently a hydrogen atom or an alkyl group; and
n and m are each an integer of 2.

11. The organic semiconductor transistor according to claim 10, wherein the alkyl group is an alkyl group having 1 to 20 carbon atoms.

12. The organic semiconductor transistor according to claim 10, wherein the alkyl group is a straight-chain or branched alkyl group.

13. The organic semiconductor transistor according to claim 10, wherein the two Rs in Formula (III) are the same.

14. The organic semiconductor transistor according to claim 1, wherein
the plurality of electrodes comprise a source electrode, a drain electrode, and a gate electrode;
the organic semiconductor transistor further comprises an insulation layer;
the gate electrode is separated from both of the source electrode and the drain electrode;
the organic semiconductor layer is in contact with both of the source electrode and the drain electrode;
the insulation layer is sandwiched between the organic semiconductor layer and the gate electrode; and
the organic semiconductor transistor is a field effect transistor.

15. An organic semiconductor transistor comprising:
a plurality of electrodes; and
an organic semiconductor layer including at least one compound represented by the following Formula (I),

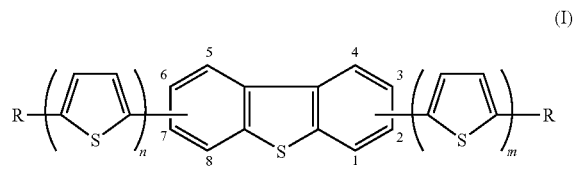

wherein, in Formula (I),
each R is independently a hydrogen atom or an alkyl group;
n and m are each independently an integer of 1 to 3; and
n and m are not the same integer.

* * * * *